(12) United States Patent
Clair et al.

(10) Patent No.: US 7,399,747 B1
(45) Date of Patent: Jul. 15, 2008

(54) PEPTIDES CARRYING SUBSTANCES ACROSS THE BLOOD BRAIN BARRIER

(75) Inventors: Philippe Clair, Nimes (FR); Michel Kaczorek, Montferrier-sur-Lez (FR); Jamal Temsamani, Nimes (FR)

(73) Assignee: SYNT:EM, Nimes (FR)

( * ) Notice: Subject to any disclaimer, the term of this patent is extended or adjusted under 35 U.S.C. 154(b) by 0 days.

(21) Appl. No.: 09/857,000

(22) PCT Filed: Nov. 26, 1999

(86) PCT No.: PCT/FR99/02938

§ 371 (c)(1),
(2), (4) Date: Sep. 7, 2001

(87) PCT Pub. No.: WO00/32236

PCT Pub. Date: Jun. 8, 2000

(30) Foreign Application Priority Data

Nov. 30, 1998 (FR) .................................. 98 15074

(51) Int. Cl.
*A61K 38/00* (2006.01)
*C07K 5/00* (2006.01)

(52) U.S. Cl. ............................ 514/15; 514/13; 424/9.1; 530/326; 530/328; 435/325

(58) Field of Classification Search .................. 514/13, 514/15; 530/326, 328; 435/325, 252.1, 254.1, 435/253.5; 424/9.1
See application file for complete search history.

(56) References Cited

FOREIGN PATENT DOCUMENTS

| WO | WO-97/12912 | * | 4/1997 |
| WO | WO-99/07728 | * | 2/1999 |

OTHER PUBLICATIONS

Derossi et al., J. Biol. Chem. 269 (14), 10444-50 (1994).*
Rousselle, C., et al., "New Advances in the Transport of Doxorubicin Through The Blood-Brain-Barrier by a Peptide Vector-Mediated Strategy", Mol. Pharamacol., 57, 679 (2000), abstract only.
Rousselle, C., et al., "Enhanced Delivery of Doxorubicin into the Brain Via a Peptide-Vector-Mediated Strategy: Saturation Kinetics and Specificity", J. Pharmacol. Exp Ther., 296, 124 (2001), abstract only.
Blanc, E., et al., "Peptide-Vector Strategy Bypasses P-Glycoprotein Efflux, and Enhances Brain Transport and Solubility of Paclitaxel", Anticancer Drugs., 15, 947-954 (2004).
Rousselle, C., et al., "Improved Brain Delivery of Benzylpenicillin with a Peptide-Vector-Mediated Strategy", J Drug Target., 10, 309-315 (2002).
Temsamani, J., et al., "Improved Brain Uptake and Pharmacological Activity Profile of Morphine-6-Glucuronide Using a Peptide Vector-Mediated Strategy", J Pharmacol. Exp Ther., 313, 712, (2005), abstract only.
Rousselle, C., et al., "Improved Brain Uptake and Pharmacological Activity of Dalargin Using a Peptide-Vector Mediated Strategy", J Pharmacol. Exp Ther., 306, 371 (2003), abstract only.
Guidance for Industry, "Estimating the Maxiimum Safe Starting Dose in initial Clinical Trials for Therapeutics in Adult Healthy Volunteers" US Dept. Health and Human Services, Jul. 2005, Pharmacology and Toxicology, Internet accessalbe at http://www.fda.gov/cder/guidance/index.htm.

* cited by examiner

*Primary Examiner*—Chih-Min Kam
(74) *Attorney, Agent, or Firm*—Oblon, Spivak, McClelland, Maier & Neustadt, P.C.

(57) ABSTRACT

The invention concerns the use of a linear peptide paired with an active substance for diagnosing or treating a CNS pathology by preparing a medicine capable of crossing the blood brain barrier to be used for diagnosis or treatment of a pathology localized in the CNS.

4 Claims, 15 Drawing Sheets

FIGURE 1: Preparation of doxorubicin-Succ-peptides

FIGURE 2: Preparation of doxorubicin-SMP-3MP-peptides

PENETRATION OF DALARGINE INTO THE BRAIN

FIGURE 8

ANALGESIC ACTIVITY OF VECTORIZED DALARGINE

Latency (sec.)

| Group | Latence (sec) | | | | | | |
|---|---|---|---|---|---|---|---|
| | 0min | 5min | 10min | 15min | 30min | 45min | 90min |
| Dalargin | 4 | 7.6 | 5.1 | 5.6 | 4.8 | 5.6 | 5.3 |
| Dal-SynB1 | 5 | 22.75 | 14.75 | 13.25 | 7.75 | 4 | 5.5 |
| SynB1 | 6.1 | 6.8 | 7.5 | 5.5 | 4.67 | 5 | 5.17 |

PENETRATION OF PRODUCTS INTO THE BRAIN

DISTRIBUTION OF PRODUCTS INTO BRAIN STRUCTURES

DISTRIBUTION OF PRODUCTS AFTER CAPILLARY DEPLETION

Synthesis of N-Benzyl-Penicillin-SynB1

PENETRATION OF PENICILLIN INTO THE BRAIN

DISTRIBUTION OF PRODUCTS INTO BRAIN STRUCTURES

PEPTIDES CARRYING SUBSTANCES ACROSS THE BLOOD BRAIN BARRIER

This application is a national stage of PCT/FR99/02938, filed Nov. 26, 1999, which claims the benefit of FRANCE 98/15074, filed Nov. 30, 1998.

The present invention relates to the use of peptides as vectors for the transfer of active molecules through the hemato-encephalic barrier (HEB) for applications in therapy and in diagnosis.

The major problem in the treatment of many diseases in the central nervous system lies in the fact that the administered molecules do not go past the hemato-encephalic barrier and therefore cannot reach their target in the brain.

Endothelial cells that make up the HEB form an obstacle to molecules that attempt to go past them, in a number of ways. These endothelial cells form a physical barrier represented by sealed junctions that are joined together and prevent any passage through the paracellular pathway, particularly since the endocytose activity in this pathway is low which very much limits the passage of plasma substances to the cerebral extracellular space.

Therefore, one of the research priorities in this field is to find means of increasing the efficiency with which active substances pass through the HEB. Several strategies have been developed to increase passage of these substances through the HEB (Pardridge, 1994, Tibtech 12, 239-245, Tamai et al., 1996, Adv. Drug Del. Rev. 19, 401-424).

Three main strategies have been proposed for the transport of molecules through the HEB, namely a neurosurgical strategy, a pharmacological strategy for small molecules and a physiological strategy.

The neurosurgical strategy may be implemented by intraventricular infusion of the active substance, by cellular therapy, and by disturbance of the HEB. Intraventricular infusion requires that a catheter is placed in the ventricles (Aird, 1984, Exp. Neurol. 86, 342-358). This technique is very invasive and is not efficient for the transport of active substances in the parenchyma. Disturbance of the HEB causes a transient opening of tight junctions, in the case of vasoactive substances such as leukotrienes or bradykinines (Baba et al., 1991, J. Cereb. Blood Flow Metab. 11, 638-643). This strategy is also invasive and requires an arterial access in sedated patients. Furthermore, a repeated disturbance of the HEB can result in neuropathic changes (Salahuddin et al., 1988, Acta Neuropathol. 76, 1-10).

The pharmacological strategy for the transport of small molecules includes the addition of lipidic groups and the use of liposomes (Zhou et al., 1992, J. Controlled Release 19, 459-486). The addition of a lipidic group enables chemical conversion of molecules soluble in water into molecules soluble in lipids. However, synthesis of this type of product results in molecules that exceed the transport threshold. The molecules must have a molecular weight of less than 600 d otherwise they will not go past the HEB. This is why liposomes, or even small vesicles, are too large and consequently inefficient for transport through the HEB (Levin, 1980, J. Med. Chem. 23, 682-684; Schackert et al., 1989, Selective Cancer Ther. 5, 73-79).

The physiological strategy makes use of a receiver-dependent transport system. The molecule to be transported is coupled to a biological molecule that has a receiver in the HEB. For example, transferrin has a receiver in the HEB and may be used as a vector (Jeffries et al., 1984, Nature 312, 162-163; Friden et al., 1983, Science 259, 373-377; Friden, 1994, Neurosurgery 35, 294-298). Although this strategy enables an increase in the passage of molecules through the HEB, it does have some disadvantages. Firstly, coupling between the molecule and the vector takes place through genetic methods thus restricting the number of molecules to be transported to polypeptides or proteins only. Furthermore, the coupling system of the molecule to the vector is complicated.

Therefore, this invention is designed to overcome these disadvantages using peptides to carry substances through the hemato-encephalic barrier (HEB). There are several advantages to this approach. Firstly, the vector peptide is chemically synthesized. Furthermore, most molecules used for medicines (conventional molecules, peptides, proteins, oligonucleotides) can be easily and efficiently coupled to the vector.

Prior art described many peptides capable of passing through eukaryote cell membranes very quickly, such as the following peptides: Protegrine, Antennapedia, Tachyplesine, Transportan, etc.

Some of these have cytolytic properties. These peptides, called antibiotic peptides, particularly include Protegrins and Tachyplesins. Protegrins and Tachyplesins are natural antibiotic peptides which have a hairpin type structure held in place by disulfide bonds. These bonds play an important role in the cytolytic activity observed on human cells.

Depending on their structure, antibiotic peptides may be classified in three main families:

Antibiotic peptides with amphipathic alpha helices: cecropins and maganins (Maloy, W. L. et al., 1995, BioPolymer 37, 105-122).

Antibiotic peptides with beta platelets joined together by disulfide bonds: defensins (Lehrer, R. I. et al., 1991, Cell 64:229-230; Lehrer, R. I. et al., 1993, Ann. Rev. Immunol. 11:105-128), protegrins (Kokryakov, V. N. et al., 1993, FEBS 337:231-236), tachyplesins (Nakamura, T. et al., 1988, J. Biol. Chem. 263:16709-16713; Miyata, T. et al., 1989, J. Biochem. 106:663-668).

Antibiotic peptides with destructured chains containing a large number of angles related to the presence of a number of prolines: bactenecins and PR39 (Frank, R. W. et al., 1991, Eur. J. Biochem. 202, 849-854).

A set of five peptides denoted PG-1, PG-2, PG-3, PG-4 and PG-5 are referred to as protegrins. The sequences of these five peptides are given below; they are closely related to and are isolated from pork leukocytes (V. N. Kokryakov & col. FEBS lett. 327, 231-236):

PG-1: RGGRLCYCRRRFCVCVGR- $NH_2$ (SEQ ID NO: 1)
PG-2: RGGRLCYCRRRFCICV- $NH_2$ (SEQ ID NO: 2)
PG-3: RGGGLCYCRRRFCVCVGR- $NH_2$ (SEQ ID NO: 3)
PG-4: RGGRLCYCRGWICFCVGR- $NH_2$ (SEQ ID NO: 4)
PG-5: RGGRLCYCRPRFCVCVGR- $NH_2$ (SEQ ID NO: 5)

Tachyplesins (Tamura, H. et al., 1993, Chem. Pharm. Bul. Tokyo 41, 978-980) denoted T1, T2 and T3 and polyphemusins (Muta, T. 1994, CIBA Found. Sym. 186, 160-174), denoted P1 and P2, for which the sequences are given below, are corresponding peptides isolated from hemolymph from two crabs, *Tachylplesus tridentatus* for tachyplesins T1, T2 and T2 and *Limmululs polyphemus* for polyphemusins P1 and P2 (SEQ ID NO: 6 and SEQ ID NO: 7 respectively).

P1: RRWCFRVCYRGFCYRKCR- $NH_2$ (SEQ ID NO: 6)
P2: RRWCFRVCYKGFCYRKCR- $NH_2$ (SEQ ID NO: 7)

Protegrins, tachyplesins and polyphemusins contain a large proportion of basic residues (lysines and arginines) and have four cysteines which form two parallel disulfide bonds.

These three families of peptides also have similarities with some defensins, and in particular with human defensin NP-1 (Kokryakov, V. N. et al., 1993, Febs Let. 327, 231-236).

Thus, within the framework of this research work, the Applicant has discovered that an irreversible reduction of these disulfide bonds can result in linear peptides, hereinafter referred to as "Pegelines", which have the property of being able to quickly passing through membranes in mammal cells by means of a passive mechanism that does not involve a membrane receiver. These linear peptides are non-toxic and have no lytic activity, and consequently they form a new carrier system for active substances in therapeutic or diagnosis domains. The work and results concerning these linear peptides and their use as a vector for active substances are described in the French patent application No. 97/10297 submitted by the Applicant on Aug. 12, 1998.

Peptides derived from the Antennapedia family are derivatives of the Antennapedia homeodomain transcription factor of drosophilae and, for example, are described in PCT international patent applications published under numbers WO91/18981 and WO97/12912. The sequence of these peptides has the specific feature that it is strongly conserved in all homeoproteins. These peptides are composed of three alpha helices and are capable of passing through the cellular membrane. The smallest homeodomain moiety capable of passing through membranes is a peptide of 16 amino acids (Prochiantz, 1996, Curr. Opin. In Neurob. 6, 629-634; Derossi et al., 1994, J. Biol. Chem. 269, 10444-10450).

Research work done within the framework of this invention has now enabled the applicant to show that some of these linear peptides, in other words peptides without a disulfide bond, may be used as a very efficient vector capable of passing through the HEB carrying an active substance for diagnosis or therapy of a disorder affecting the central nervous system (CNS).

Therefore, the invention more particularly relates to the use of a linear peptide coupled to an active substance for diagnosis or therapy of a disorder affecting the CNS for the preparation of a medicine capable of passing through the hematoencephalic barrier to be used for diagnosis or therapy of a disorder localized in the CNS, the said peptide satisfying one of the following formulas (I), (II) or (III):

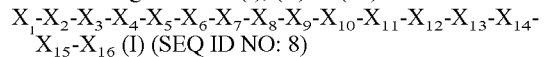

In formula (I), the residues $X_1$ to $X_{16}$ are residues of amino acids, in which 6 to 10 of them are hydrophobic amino acids and $X_6$ is tryptophan,

In formulas (II) and (III):
  groups B may be identical or different, and represent an amino acid residue for which the side chain carries a basic group, and
  groups X may be identical or different, and represent a residue of aliphatic or aromatic amino acid.

The said peptides with formulas (I), (II), (III) in retro form, composed of amino acids with a D and/or L configuration, or a moiety of these acids composed of a sequence of at least five and preferably at least seven successive amino acids of peptides with formulas (I), (II) or (III), obviously provided that this moiety has vector properties with no toxicity for the cells.

Peptides with formula (I) are derived from the Antennapedia family. In peptides with formula (I), the hydrophobic amino acids are alanine, valine, leucine, isoleucine, proline, phenylalanine, tryptophan, tyrosine and methionine, and the other amino acids are:

non-hydrophobic, possibly non-polar amino acids such as glycine, or polar such as serine, threonine, cysteine, asparagine, glutamine, or
acid (aspartic or glutamic acid), or
basic (lysine, arginine or histidine), or
an association of amino acids in these three categories.

The preferred formula (I) type peptides include 6 hydrophobic amino acids and 10 non-hydrophobic amino acids.

Linear formula (II) type peptides are derived from the Protegrin family and linear formula (III) type peptides are derived from the Tachyplesin family. The preferred peptides with formula types (II) and (III) are peptides in which:
  B is chosen among arginine, lysine, diaminoacetic acid, diaminobutyric acid, diaminopropionic acid, ornithine and
  X is chosen among glycine, alanine, valine, norleucine, isoleucine, leucine, cysteine, cysteine$^{Acm}$, penicillamine, methionine, serine, threonine, asparagine, glutamine, phenylalanine, histidine, tryptophan, tyrosine, proline, Abu, carboxylic amino-1-cyclohexane acid, Aib, carboxylic 2-aminotetraline, 4-bromophenylalanine, tert-Leucine, 4-chlorophenylalanine, beta-cyclohexylalanine, 3,4-dichlorophenylalanine, 4-fluorophenylalanine, homoleucine, beta-homoleucine, homophenylalanine, 4-methylphenylalanine, 1-naphthylalanine, 2-naphthylalanine, 4-nitrophenylalanine, 3-nitrotyrosine, norvaline, phenylglycine, 3-pyridylalanine, [2-thienyl]alanine.

In peptides with type (I), (II) or (III) formulas, B, X and $X_1$ to $X_{16}$ may be natural or non-natural amino acids, including amino acids with D configuration.

The preferred peptides used according to the invention are chosen from among peptides with the following amino acid sequences:
  RGGRLSYSRRRFSTSTGR (SEQ ID NO: 11), also denoted SynB 1 in the following,
  RRLSYSRRRF (SEQ ID NO: 12), also denoted SynB 3 in the following,
  rqikiwfqnrrrmkwkk (SEQ ID NO: 13)

where the lower case letters represent amino acids in d form.

The active substance may be coupled with a peptide defined above in the compositions according to the invention by any acceptable bonding means considering the chemical nature, the size and number of active substances and associated peptides. They may be covalent, hydrophobic or ionic bonds, or cleavable or non-cleavable bonds in the physiological media or inside cells.

Coupling may be achieved in any site in the peptide in which functional groups such as —OH, —SH, —COOH, —NH$_2$ are naturally present or have been introduced. Thus an anticancer agent may be related to the peptide at the N-terminal or C-terminal ends, or in the peptide side chains.

Similarly, coupling may be achieved on any site in the active substance, for example at which functional groups such as —OH, —SH, —COOH, —NH$_2$ are naturally present or have been introduced.

Thus, the invention is particularly related to the use of compounds according to the formula (IV) below:

where
  A is a peptide as described above,
  B is a substance active in diagnosis or therapy for a disorder of the CNS,
  n is 1 or more, and preferably up to 10, and advantageously up to 5, (−)$_m$ represents the linker between A and B, where m is 1 or more, and preferably up to 10 and advantageously up to 5, for the preparation of a medicine capable of passing through the hemato-encephalic barrier to be used in diagnosis or therapy for a disorder localized in the CNS.

In formula (IV), the (−)$_m$ linker between A and B is a covalent, hydrophobic or ionic linker, cleavable or non-cleavable in physiological media or inside the cells, or a mixture thereof.

Compounds with a type (IV) formula may be prepared by chemical synthesis or by using molecular biology techniques.

Chemical syntheses can be carried out using commercial devices capable of incorporating non-natural amino acids such as D enantiomers and residues with lateral chains for which the hydrophobicities and sizes are different from those of their natural homologues. During synthesis, it is obviously possible to make a wide range of modifications, for example such as introducing a lipid such as prenyl or myristyl on the N-terminal, so that the peptide according to the invention, and therefore the compound with a type (IV) formula, can be anchored to a lipidic membrane such as a liposome membrane composed of lipids. One or several peptidic linkers (—CO—NH—) can also be replaced by equivalent structures like —CO—N(CH$_3$)—, —CH$_2$—CH$_2$—, —CO—CH$_2$—, or groups such as —CH$_2$—, —NH—, —O— can be inserted.

It would also be possible to obtain compounds with a type (IV) formula, or some of these compounds with a proteic nature, starting from an encoding nucleic acid sequence. Another purpose of this invention is a nucleic acid molecule comprising or composed of an encoding nucleic sequence for a linear peptide derived from an antibiotic peptide. More particularly, the invention relates to a nucleic acid molecule comprising at least one encoding sequence for a compound with formula (IV) or a part of it with the proteic nature. These nucleic acid sequences may be DNAs or RNAs and may be associated with control sequences and/or inserted in vectors. The vector used is chosen as a function of the host into which it will be transferred; it may be any vector like a plasmid. These nucleic acids and vectors are useful to produce peptides and compounds with formula (IV) or part of them with the proteic nature in a cellular host. Preparation of these vectors, and production or expression of peptides or compounds with a type (IV) formula in a host, may be achieved using molecular biology and genetic engineering techniques well known to those skilled in the art.

Compositions containing compounds with a type (IV) formula, and advantageously a pharmaceutically acceptable carrier, may be administered by different pathways, for example (non-limitatively) intravenous, intra-muscular, subcutaneous pathways, etc.

Peptides with a type (I), (II) or (III) formula can be used to make an active substance pass through the hemato-encephalic barrier, even though the substance would not pass through the barrier otherwise, or would pass through it very ineffectively. Therefore they can be used for the treatment, prevention or diagnosis of a disorder affecting the CNS (as previously proposed), but also for studies carried out on a variety of drugs with hemato-encephalic barrier models.

Active substance included within the invention include particularly proteins such as polypeptides or peptides, antibodies or parts of antibodies, nucleic acids and oligonucleotides or ribozymes, and obviously active chemical molecules for the treatment or prevention of human or animal pathologies of the CNS, such as for example (but not restrictively) antitumoral, antiviral, antidepression agents, analgesic agents, etc.

For diagnosis purposes, the active substance may be a radioactive marker or a coloured marker, or any other means or substance capable of revealing a metabolism or pathology affecting the CNS.

Some examples of CNS disorders for which this invention could be used for diagnosis, treatment or prevention, are brain cancer, Alzheimer's disease, Parkinson's disease, depression, pain, meningitis, etc., but this list is in no way limitative.

Therefore, the invention relates particularly to the use of compounds according to formula (IV) for the preparation of a medicine intended for the treatment or prevention of brain cancers, Alzheimer's disease, Parkinson's disease, depression, pain, meningitis.

Other advantages and characteristics of the invention will become clear after reading the following examples concerning the preparation of compounds with a type (IV) formula in which the active substances are doxorubicin, dalargine, penicillin and their penetration into the brain in accordance with the use of linear peptides according to the invention.

BRIEF DESCRIPTION OF DRAWINGS

FIG. 8 shows analgesic activity of vectorized dalargine.

EXAMPLE I

Penetration of Doxorubicin

I—Experimental Conditions

1) Chemical Synthesis

Several peptides were synthesized and internalisation was tested in several cellular lines. In general, the physicochemical properties of the peptides were modified and the results obtained show that some peptides penetrate much better than others after the modification, like peptides in compounds No. 1 and 2 in table I below. It was also observed that some peptides penetrate more quickly into some cellular types than into others, which indicates a cellular tropism.

a) Preparation of Doxorubicin-Succ-Peptides

Figure 1:
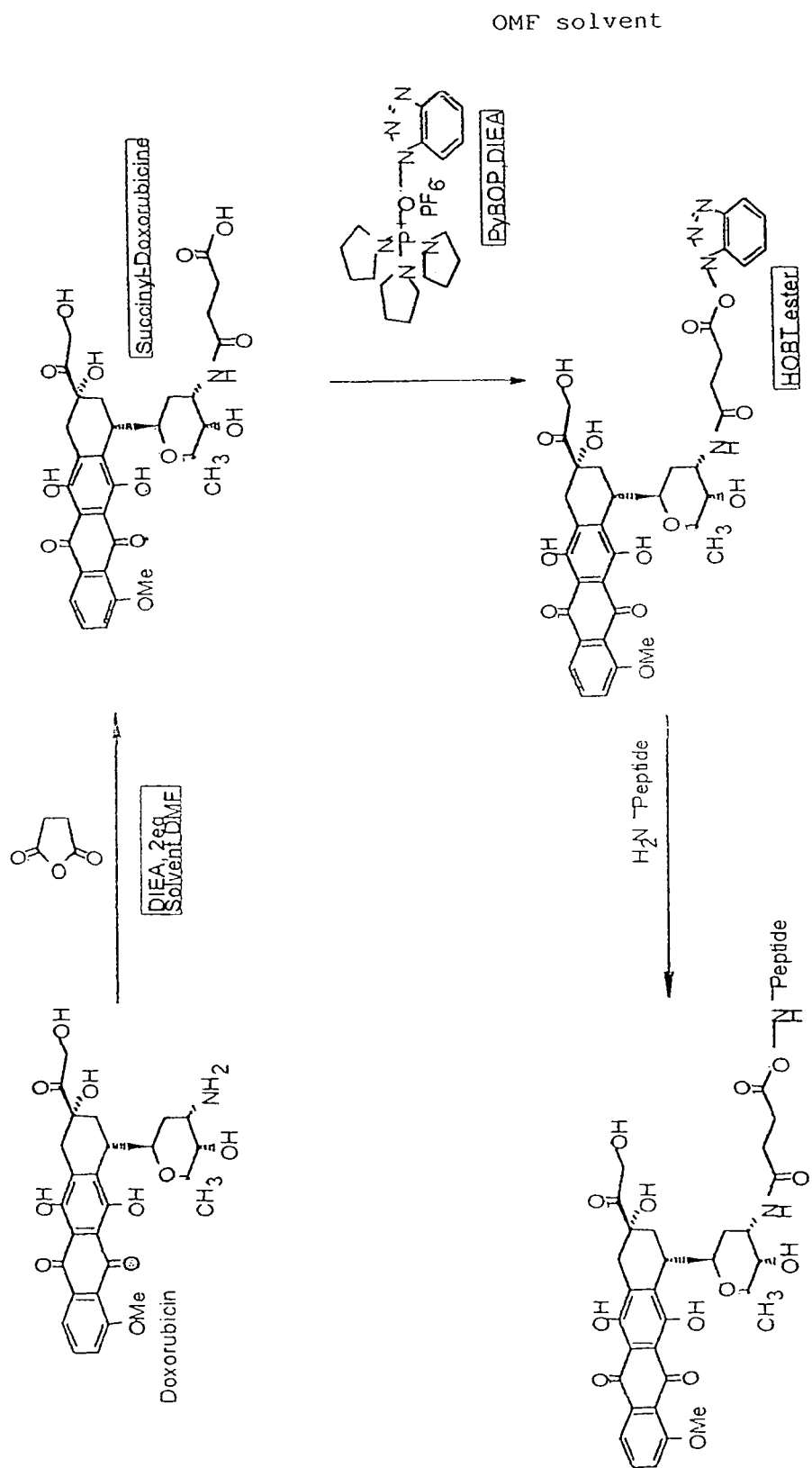
FIG. 1 shows preparation of doxorubicin-Succ-peptides.

Doxorubicin is coupled on a peptide through a succinic link in three steps as shown in FIG. 1 attached.

Succinic anhydride (1, leq, dissolved in DMF) is added to doxorubicin chlorydrate (1 eq), solubilised in dimethylformamide (DMF) in the presence of Disopropylethylamine (DIEA, 2 eq).

After 20 minutes incubation at room temperature, the doxorubicin hemisuccinate thus formed is then activated by the addition of PyBOP (Benzotriazol-1-yl-oxopyrrolidine-phosphonium hexafluorophosphate 1.1 eq in DMF) and DIEA (2 eq). This second reactional mix is incubated for 20 minutes.

The peptide (1.2 eq in DMF) is then added to the reactional mix and spontaneously combines with doxorubicin hemisuccinate activated during an additional 20 minutes incubation.

The coupling product is then purified on HPLC (high pressure liquid chromatography) in preparation, and is then freeze dried.

Each of the steps, and the final product, are checked by analytic HPLC and mass spectrometry.

b) Preparation of Doxorubicin-SMP-3MP-Peptide

Figure 2:
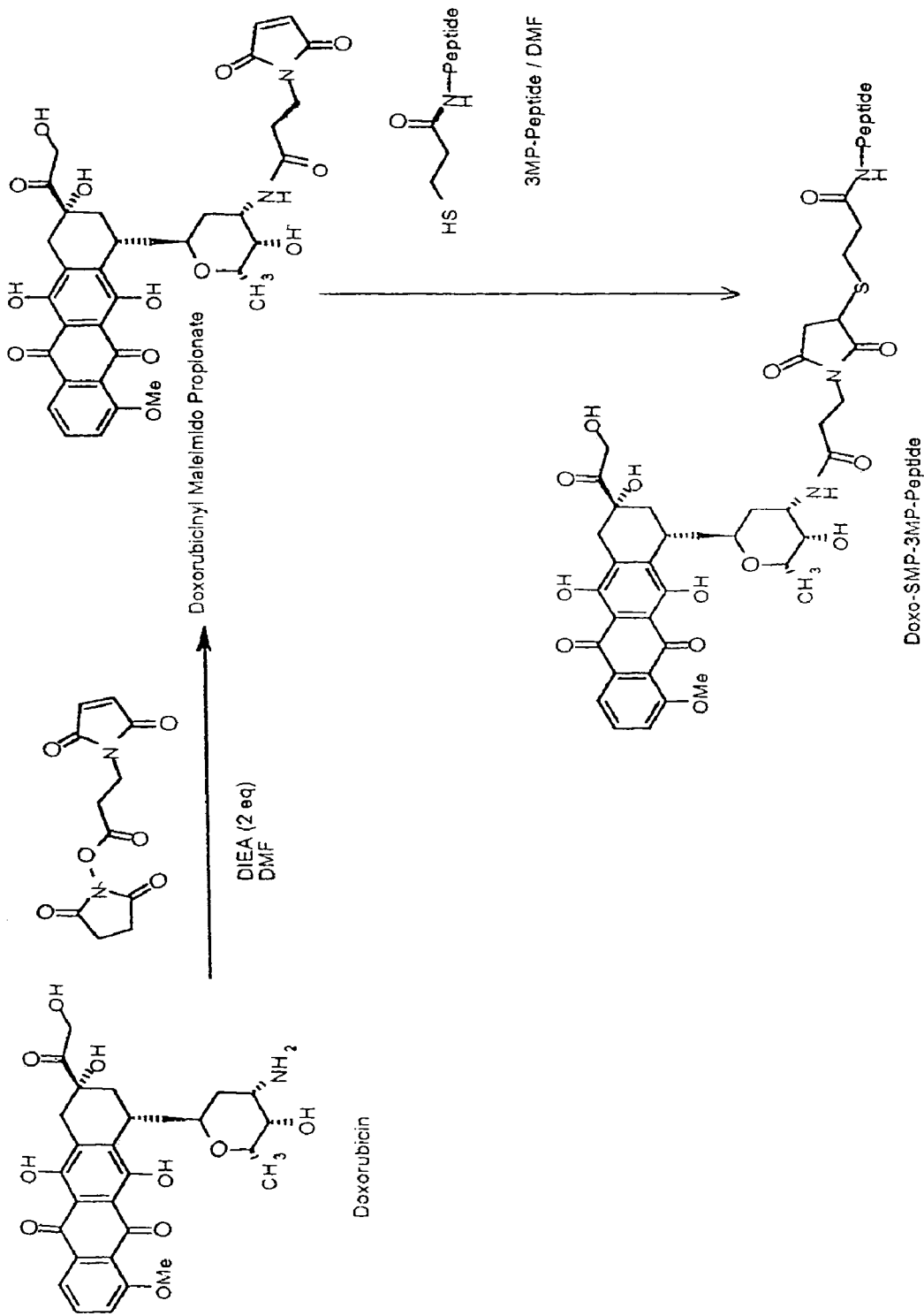
FIG. 2 shows preparation of doxorubicin-SMP-3MP-peptides.

The doxorubicin is coupled on a thiol function carrier peptide in two steps as shown in FIG. 2 attached.

N-hydroxy-Succinimidyl-Maleimido-Propionate (SMP, 1 eq dissolved in DMF) is added to doxorubicin chlorhydrate (1 eq) solubilised in dimethylformamide (DMF) in the presence of Disopropylethylamine (DIEA, 2 eq).

The thiol function carrier peptide (1.2 eq in DMF) is then added to the reactional mix, and spontaneously combines with doxorubicin maleimidopropionate during an additional 20 minutes incubation.

The coupling product is then purified on HPLC in preparation and then freeze dried.

Each of the steps, and the final product are checked by analytic HPLC and mass spectrometry.

2) Products Tested

The products tested are shown in table I below.

TABLE I

| Compound | | SEQ ID NO: |
|---|---|---|
| No. 1 (Doxo-Syn-B1) | Doxo-CO—(CH2)2—CO-RGGRLSYSRRRFSTSTGR | RGGRLSYSRRRFSTSTGR (SEQ ID NO:11) |
| No. 2 (Doxo-SMP-3MP-peptide with amino acids in d form) | Doxo-SMP-3MP-rqikiwfqmrrmkwkk | rqikiwfqmrrmkwkk (SEQ ID NO:13) | doxo=doxorubicin

CO—(CH2)$_2$—CO=succinate linker

SMP-3MP=Succinimydyl Maleimido-Propionate-3-MercaptoPropionate linker

Lower case letter=Amino acids in d form.

3) In Situ Cerebral Perfusion a) Perfusion

This is a fast and sensitive method of evaluating the penetration of various compounds into the central nervous system (Takasato et al., 1984, Am. J. Physiol. 247, 484-493; Allen et al., 1997, Pharm Res. 14, 337-341). Two month old male Sprague-dawley rats (250-350 g. Iffa-Credo; l'Arbresle, France) are anaesthetised. After exposure of the common carotid, the right external carotid artery is bound at the junction with the internal carotid and the common carotid is bound between the heart and the site at which the catheter is installed (polyethylene catheter, ID=0.76). This catheter, previously filled with a solution of heparin (100 units/ml) is inserted into the common carotid. Rats are perfused with the perfusion buffer (128 mM NaCl, 24 mM NaHCO$_3$, 4.2 mM KCl, 2.4 mM NaH$_2$PO$_4$, 1.5 mM CaCl$_2$, 0.9 mM MgSO$_4$, and 9 mM D-glucose). This buffer is filtered and then is bubbled using a mix containing 95% O$_2$/5% CO$_2$ in order to keep the pH close to 7.4 and to supply oxygen to the brain during the perfusion.

The rats are perfused with the buffer containing free doxorubicin or compounds No. 1 or 2. The doxorubicin is radio-marked with carbon 14 in each product (specific activity=9.4 microCi/mg, Amersham, France). The products are perfused at a concentration of 0.33 microCi/ml or 0.035 mg/rat.

The heart is stopped by cutting the ventricles immediately before perfusion starts, in order to prevent reflux of the perfusate during the perfusion. The right hemisphere is then perfused at a rate of 10 ml/min for 60 seconds, and the rat is then decapitated.

b) Rinsing

For rats on which the rinsing step is carried out, the catheter is inserted into the common carotid as described above, and is then connected to a 4-way valve (opposite passages) (Hamilton, USA) connected to two syringes; one containing the radio-marked tracer (syringe A) and the other the buffer alone (syringe B). Once the catheter is in position and the connections have been made correctly, the thoracic cage of the rat is opened and the heart is cut. The contents of syringe A are then immediately perfused at a rate of 10 ml/min. After 60 seconds, the contents of syringe B are injected in turn at the same rate. The rat is decapitated after 30 seconds of rinsing.

c) Dissection of the Brain

The brain is removed quickly after decapitation. The brain is dissected on a mirror into 8 regions, namely Hypothalamus (HY), frontal Cortex (CF), Mesencephale (MS), Occipital Cortex (CO), Parietal Cortex (CP), Thalamus (TH), Hippocampus (HP), Striatum (ST), which are placed in previously calibrated glass flasks and then weighed. These structures and 50 microliters of perfusate are digested for two hours in 1 ml of soluene at 60° C. A scintillating cocktail (10 ml, Pico-fluor, Packard) is added to each sample and the quantity of tracers contained in them is measured by double counting in liquid scintillation (Packard, Tricarb, 1900TR).

d) Capillary Depletion

This method is used to measure the distribution of products between the cerebral parenchyma and endothelial cells, Triguero et al., 1990, J. Neurochem. 54, 1882-1888). After 60 seconds of perfusion, that may or may not be followed by 30 seconds rinsing, the right hemisphere is removed, its meninges and choroid plexus are removed, and it is then homogenized in 3.5 ml of Hepes buffer (10 mM of Hepes, 141 mM of NaCl, 4 mM of KCl, 1 mM of NaH$_2$PO$_4$, 2.8 mM of CaCl$_2$, 1 mM of MgSO$_4$ and 10 mM of D-glucose, pH=7.4). After grinding in the potter, 4 ml of solution containing 4% of Dextran (PM=76900) are added and the mix is stirred vigorously in order to obtain a final concentration of 20%. All these operations are carried out at 4° C. in less than 5 minutes. After taking a sample of the homogenate thus obtained, the homogenate is then put into the centrifuge for 15 minutes at 5400 g in order to separate the endothelial cells present in the base of the cerebral parenchyma that remained in the floating material. The results are expressed as distribution volumes in the floating material and the base.

4) Intravenous Injections

NMRI-nude mice are injected intravenously with compound No. 1 or doxorubicin alone at a dose of 2.5 mg/kg (equivalent in doxorubicin). The doxorubicin is marked with carbon 14 (about 0.5 microCi is injected per mouse). The mice are sacrificed after 1, 5, 15, 30, 60, 180, 480 and 1360 minutes. The organs are then removed and counted. The quantity of radioactivity in each organ is then expressed as the quantity of product per gram of organ. In this study, we used five mice for each period of time.

In the case of compound No. 2, the CD1 mouse is injected intravenously with compound No. 2 or with free doxorubicin at a dose of 2 mg/kg (equivalent in doxorubicin). Doxorubicin is marked with carbon 14 (about 3 microCi is injected per mouse). The mouse is sacrificed after 15 minutes, 2 hours and 8 hours, and the product quantity in each organ is analysed using the "Whole-body autoradiography" technique. The quantity of radioactivity in each organ is then expressed as a quantity of product per gram of organ. We used one mouse per group in this experiment.

II—Results

1) In Situ Cerebral Perfusion a) Tolerance to Products

Initially, the effect of the tested products on the integrity of HEB was observed based on the distribution volume of [$^3$H]-sucrose, which is a small molecule that does not enter the central nervous system for short exposure times. It is estimated that this volume must not exceed 18 μg/ml. For larger volumes, it is concluded that the permeability of HEB is abnormal.

Doxorubicin, compounds numbers 1 and 2 were injected in the presence of sucrose and the integrity of the HEB is measured. Table II below shows the effect of the perfusion of the products on the integrity of the HEB.

TABLE II

| Compound | Perfused dose | State of the HEB |
|---|---|---|
| doxorubicin | 0.07 mg | Integral |
| No. 1 | 0.05 mg | Integral |
| (Doxo-SynB1) | | |
| | 0.8 mg | Integral |
| No. 2 | 0.05 mg | Integral |
| | 0.2 mg | Integral |
| | 0.8 mg | Abnormal |

Compound No. 1 does not open the HEB abnormally even at doses of 0.8 mg. However, with compound No. 2, the HEB opens at doses exceeding 0.2 mg. Consequently, the work was carried out using products at doses of 0.05 mg.

b) Product Penetration

Figure 3:
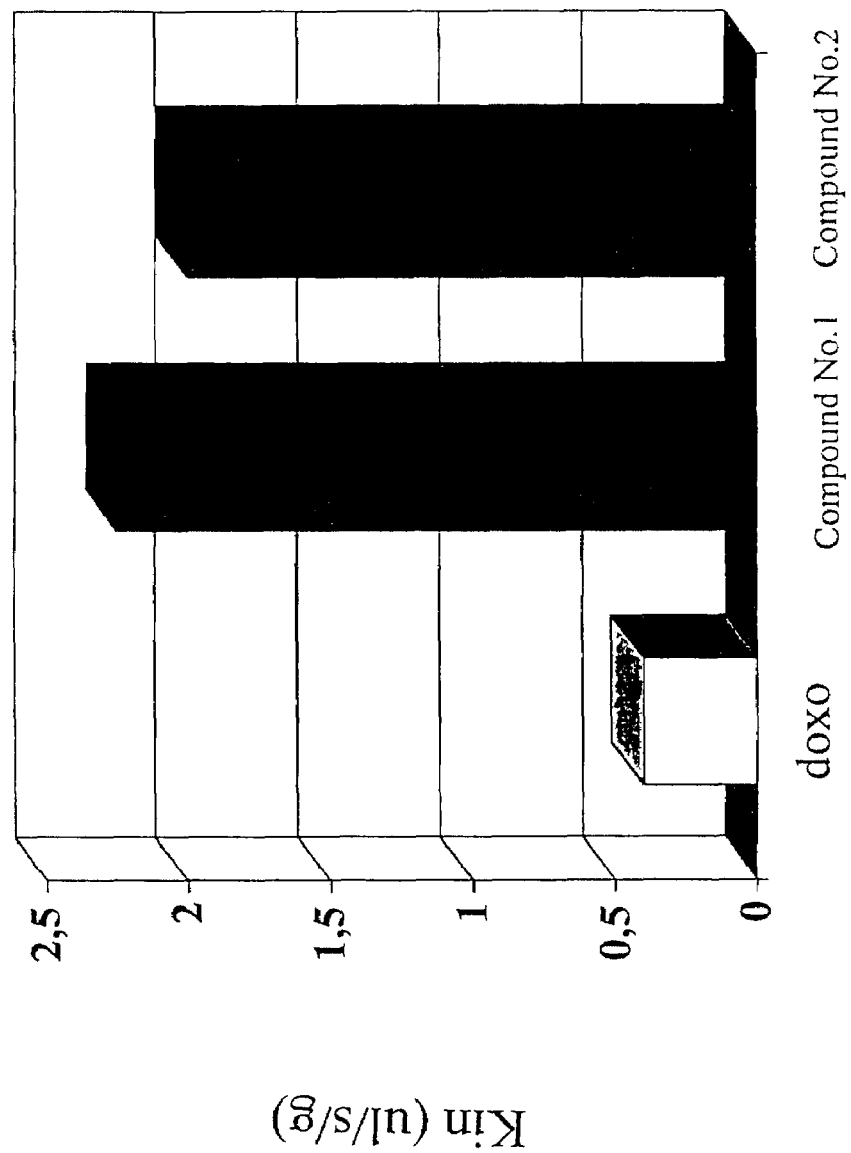
FIG. 3 shows penetration of doxorubicin, Compound No. 1 and Compound No. 2 into the brain.

This study consisted of comparing penetration in the HEB of doxorubicin alone with doxorubicin using compounds numbers 1 and 2 as vectors. After 60 seconds perfusion in the buffer, the penetration of products was estimated using the influx constant or Kin in microl/sec/g. FIG. 3 shows the penetration of products into the brain. It is observed that when doxorubicin is transported by the two vectors, its transfer into the brain is increased by 5 to 7 times after 60 seconds perfusion in the buffer.

Figure 4:
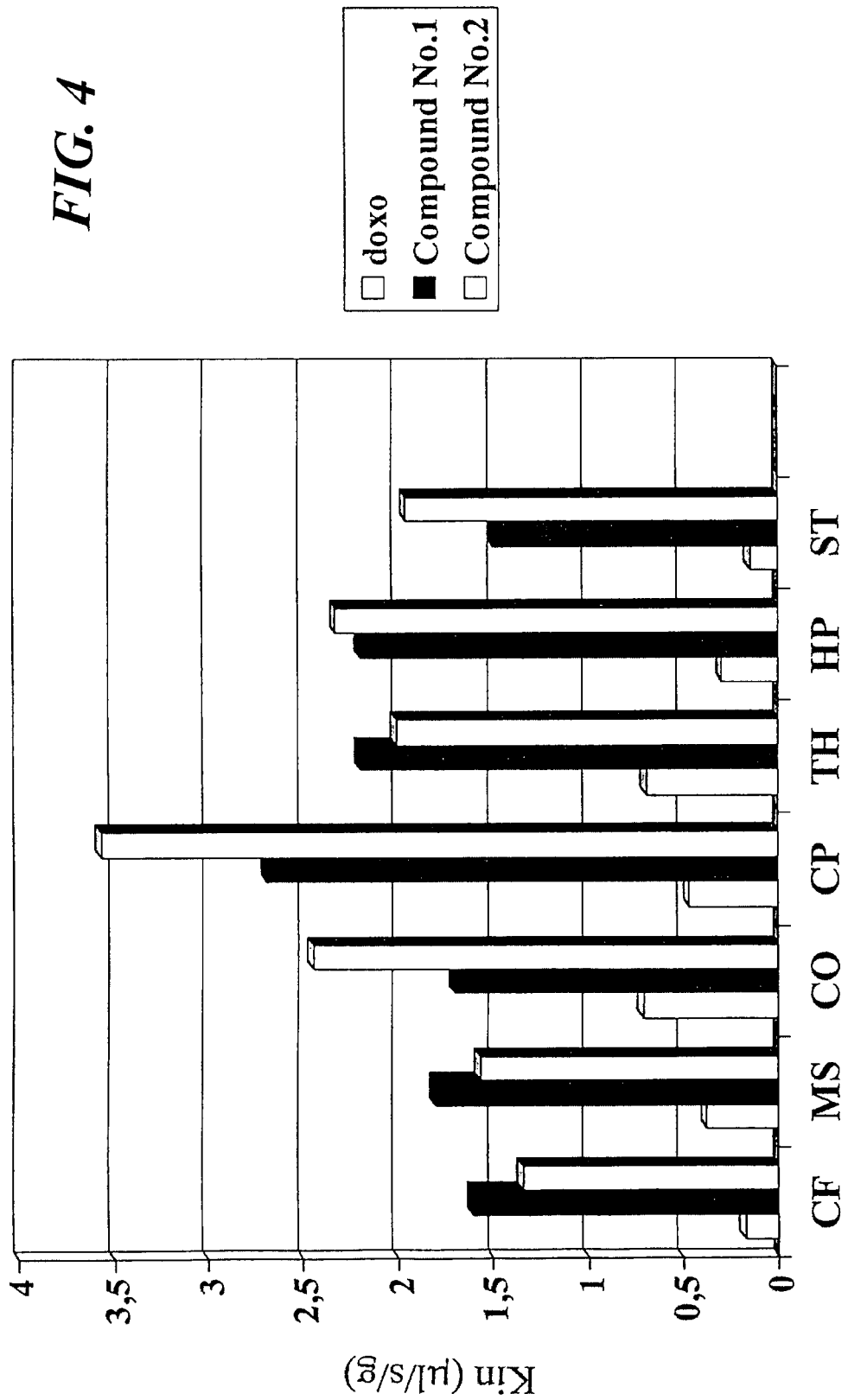
FIG. 4 shows penetration of doxorubicin, Compound No. 1 and Compound No. 2 into brain structures.

In another experiment, the brain was dissected in 8 regions as described above and the quantity of product in each region was measured. FIG. 4 attached shows the penetration of these products into the brain. It is found that penetration of compounds numbers 1 and 2 is 5 to 7 times greater than the penetration of free doxorubicin, regardless of the brain structures considered.

c) Penetration of Products After Rinsing

Figure 5:
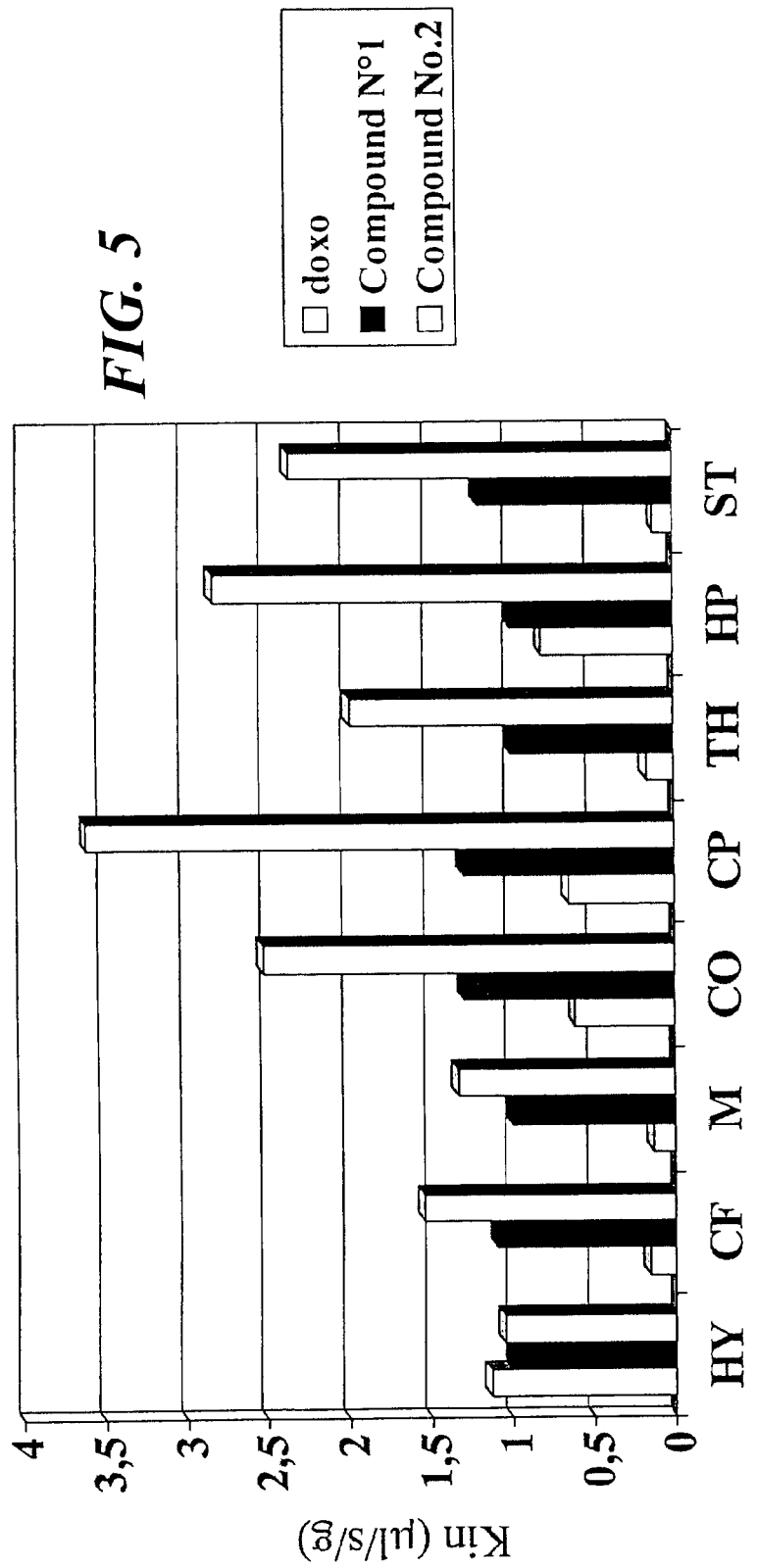
FIG. 5 shows penetration of doxorubicin, Compound No. 1 and Compound No. 2 into brain structures after rinsing.

Rinsing of cerebral capillaries by perfusion of the buffer without tracer for 30 seconds eliminates the fraction of the product being studied adhering to the luminal membrane of endothelial cells, if any. FIG. 5 attached shows the results of product penetration after rinsing. A reduction of the influx constant by about 25% is observed for free doxorubicin. For vectorised doxorubicin, this reduction is 45% for compound No. 1 and 10% for compound No. 2. Finally, penetration of compounds No. 1 and 2 is increased by factors of 4 and 7 respectively compared with free doxorubicin.

d) Distribution of Products After Capillary Depletion

This method measures the distribution of products between the cerebral parenchyma and endothelial cells. Capillary depletion is carried out after 60 seconds perfusion followed by 30 seconds rinsing. The distribution volumes (Vd) in endothelial cells and the cerebral parenchyma are expressed in microliters/g.

Figure 6:
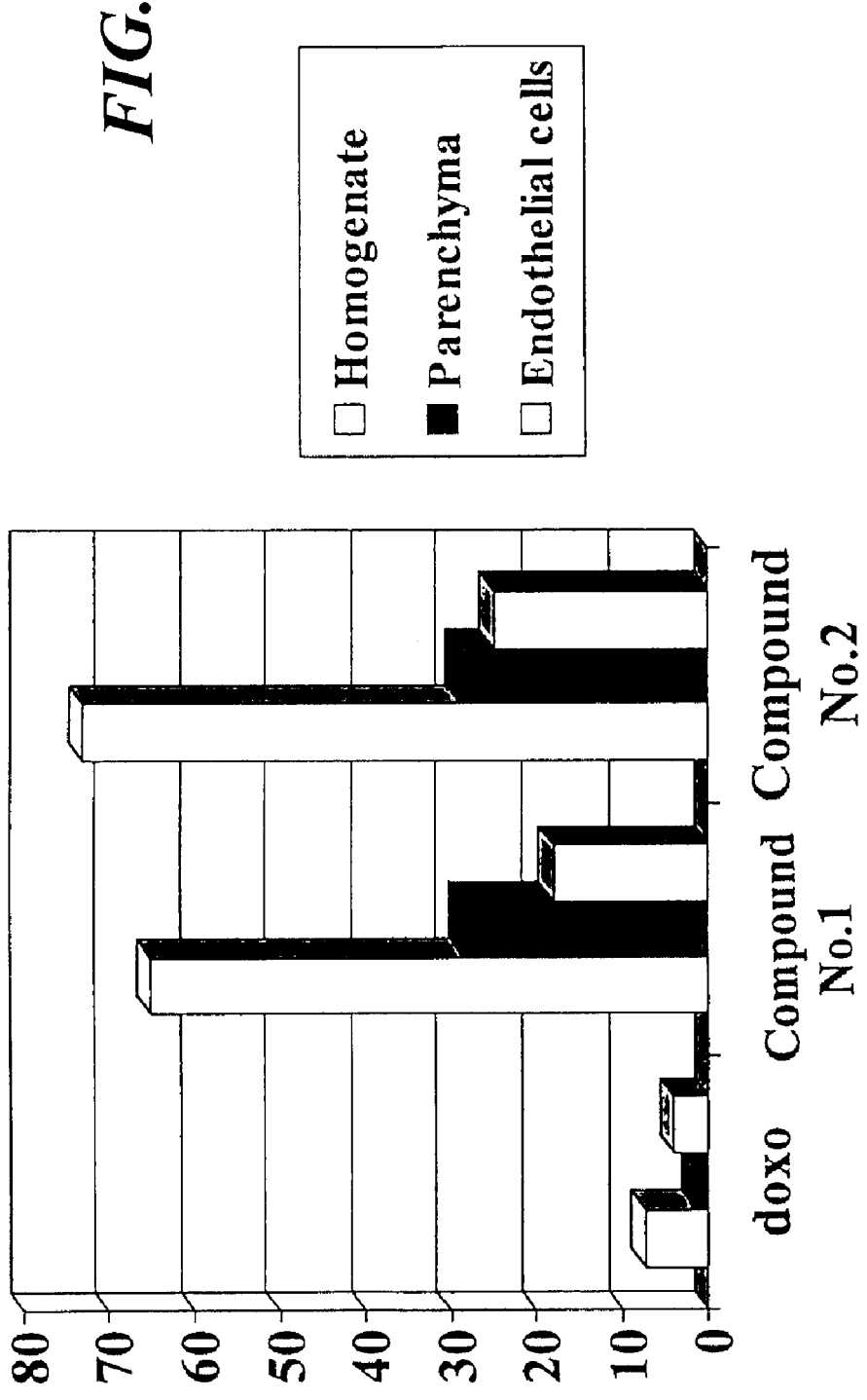
FIG. 6 shows product distribution of doxorubicin, Compound No. 1 and Compound No. 2 after capillary depletion.

FIG. 6 attached indicates the product distribution after capillary depletion. A Vd equal to 1.75 μl/g is observed for free doxorubicin in the cerebral parenchyma, the Vd for compound No. 1 is 28.5 μl/g and the Vd for compound No. 2 is 29.5 μl/g. These results show that penetration of vectorised doxorubicin (compounds No. 1 and 2) into the cerebral parenchyma is very much increased compared with the penetration of free doxorubicin. About 60% of compounds No. 1 and 2 are found in the cerebral parenchyma 1 minute after cerebral perfusion of molecules followed by 30 seconds rinsing of the cerebral capillaries.

2) Intravenous Injection

The study of a substance passing through the HEB requires the use of several complementary methods. Cerebral perfusion enables measurements over very short times. Intravenous injection can give a global evaluation of pharmacokinetics in animals over long periods. The radioactive molecule is introduced into the blood circulation and diffuses throughout the organism. A certain quantity of this molecule enters the brain, where it is measured at determined times.

a) With Compound No. 1

After intravenous injection of compound No. 1, nude mice were sacrificed at different times and the total radioactivity in the brain was counted and expressed as a quantity of product per gram of brain. Table III below shows the quantity of doxorubicin and compound No. 1 in the brain.

TABLE III

| Group | Product | Dose (mg DXR base/kg) | Time (min) | Product quantity (microg/g of brain) |
|---|---|---|---|---|
| 1 | doxorubicin | 2.5 | 1 | 0.14 |
| | | | 5 | 0.05 |
| | | | 15 | 0.04 |

TABLE III-continued

| Group | Product | Dose (mg DXR base/kg) | Time (min) | Product quantity (microg/g of brain) |
|---|---|---|---|---|
| | | | 30 | 0.05 |
| | | | 60 | 0.04 |
| | | | 180 | 0.03 |
| | | | 480 | 0.04 |
| | | | 1360 | 0.01 |
| 2 | Compound No. 1 | 2.5 | 1 | 0.48 |
| | | | 5 | 0.18 |
| | | | 15 | 0.42 |
| | | | 30 | 0.25 |
| | | | 60 | 0.12 |
| | | | 180 | 0.03 |
| | | | 480 | 0.02 |
| | | | 1360 | 0.01 |

Transport by a vector significantly improved the passage of doxorubicin through the hemato-encephalic barrier. This accumulation is observed not only for short times, but also for long periods of up to 3 hours post-administration. Table IV below shows the ratio of vectorised doxorubicin (compound No. 1) compared with doxorubicin alone.

TABLE IV

| Time (min) | Ratio of compound No. 1/doxorubicin |
|---|---|
| 1 | 3.4 |
| 5 | 3.6 |
| 15 | 10.5 |
| 30 | 5 |
| 60 | 3 |
| 180 | 1 | b) With Compound No. 2

After intravenous injection of compound No. 2, CD-1 mice were sacrificed after 15 minutes, 2 hours and 8 hours. The total radioactivity in the brain is analysed using the "Whole body autoradiography" method and is expressed as a product quantity per gram of brain. Table V below shows the quantity of doxorubicin and compound No. 2 in the brain.

TABLE V

| Group | Product | Dose (mg (DXR base/kg) | Time (min) | Product quantity (ug/g of brain) |
|---|---|---|---|---|
| 1 | doxorubicin | 2 | 15 | 1.24 |
| | | | 120 | 0.98 |
| | | | 480 | 0.67 |
| 2 | Compound No. 2 | 2 | 15 | 9.49 |
| | | | 120 | 4.73 |
| | | | 480 | 4.52 |

Transport by a vector significantly improved the passage of doxorubicin through the hemato-encephalic barrier. This accumulation was observed for long periods of up to 8 hours post-administration. Table VI below shows the ratio of vectorised doxorubucin (compound No. 2) compared with doxorubicin alone.

TABLE VI

| Time (min) | Ratio of compound No. 2/doxorubicin |
|---|---|
| 15 | 7.65 |
| 120 | 4.83 |
| 480 | 6.75 |

EXAMPLE II

Penetration of Dalargine

1) Products Tested

The products tested in this example are shown in table VII below.

TABLE VII

| Compound | | SEQ ID NO: |
|---|---|---|
| 3: dalargine | Y-(D)A-GFLR | |
| 4: dal-SynB1 | Y-(D)A-GFLR-S-S-RGGRLSYSRRRFSTSTGR | RGGRLSYSRRRFSTSTGR (SEQ ID NO:11) | dal: dalargine
S-S: linker disulfide
(D): amino acid in d form

2) Penetration of Products

This study consisted of comparing the penetration of the HEB from dalargine alone, with vectorised dalargine. Dalargine is an analgesic peptide. Dalargine was bound to the vector peptide in table VII by a disulfide bond. This form of hydrolysable bond was selected since it has been demonstrated in the literature that these disulfide bonds are stable in plasma but the bond is hydrolysed as soon as the product enters the HEB, thus releasing drugs.

Figure 7:
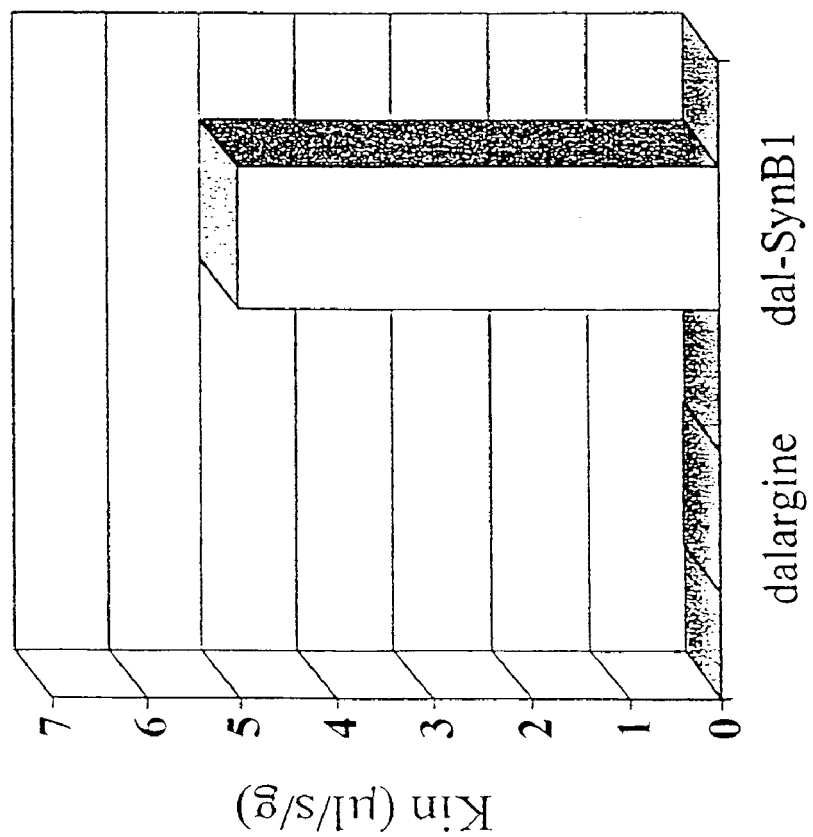
FIG. 7 shows penetration of dalargine and dal-SynB1 into the brain.

After 60 seconds perfusion in the buffer, the penetration of products is estimated by the influx constant (Kin) in μl/sec/g. FIG. 7 shows that vectorisation of dalargine by the vector peptide SynB1 considerably increases its transfer into the brain after 60 seconds perfusion in the buffer.

3) Biological Activity

For the purposes of this study, the biological activity of dalargine alone was compared with the biological activity of dalargine vectorised with SynB1. Consequently, the "Hot Plate" model in the mouse was used. In this model, the mouse is placed on a hot plate and the time that the mouse takes to react to heat is measured as the "latency time".

2 mg/Kg of each product was injected intravenously into the mouse (the dose corresponding to the quantity of dalargine). After times varying from 0 to 90 minutes, the latency time was measured. FIG. 8 shows that no effect was observed after the injection of dalargine alone. The latency time is constant. However, when vectorised dalargine is injected, an increase in the latency time is observed especially for times varying from 5 to 30 minutes after administration of the product. For example 5 minutes after injection, the latency time of vectorised dalargine is 22.75 seconds, whereas it is only 7.6 seconds for dalargine alone. This clearly shows that the analgesic activity of vectorised dalargine has been increased.

It has also been verified that this effect is not due to the peptide alone. This was done by injecting the SynB1 vector alone and measuring the latency time. The results are comparable to the results obtained with dalargine alone, indicating that the vector alone has no analgesic activity.

EXAMPLE III

Penetration of Doxorubicin

This example concerns a vector peptide other than that in example 1.

1) Products Tested

The products tested in this example are shown in table VIII below.

TABLE VIII

| Compound | | | SEQ ID NO: |
|---|---|---|---|
| Doxo | Doxorubicin | | |
| No. 5: doxo-SynB3 | Doxo-CO—(CH$_2$)$_2$—CO-RRLSYSRRRF | RRLSYSRRRF | (SEQ ID NO:12) |

Doxo: doxorubicin

CO—(CH2)$_2$—CO: linker succinate

2) Penetration of Products

Figure 9:
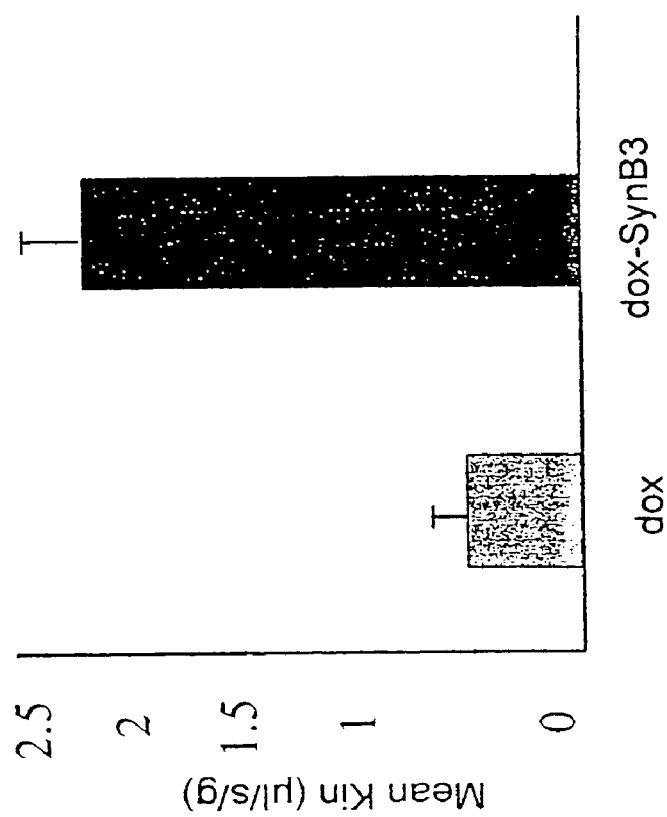
FIG. 9 shows penetration of doxorubicin and dox-SynB3 into the brain.

This study consisted of comparing the penetration of doxorubicin alone and the penetration of vectorised doxorubicin, into HEB. After 60 seconds perfusion in the buffer, the penetration of products is estimated by the influx constant (Kin) in µl/sec/g. FIG. 9 shows that vectorisation of doxorubicin by the vector peptide SynB3 increases its transfer into the brain by five times after 60 seconds perfusion in the buffer.

Figure 10:
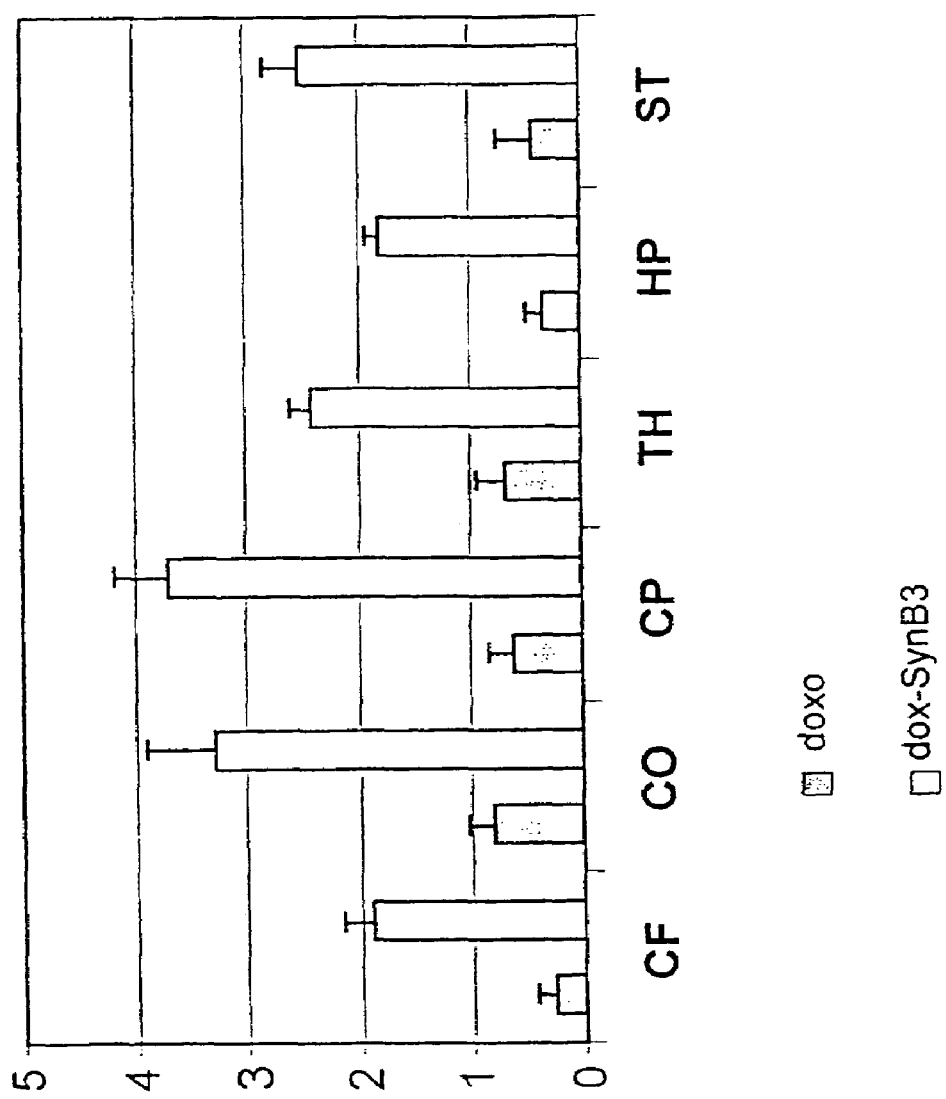
FIG. 10 shows product distribution of doxorubicin and dox-SynB3 into brain structures.

In another experiment, the brain was dissected into six regions as described above and the quantity of product in each region was measured. FIG. 10 shows that the penetration of compound No. 2 is greater than the penetration of free doxorubicin, regardless of the brain structures considered.

3) Distribution of Products After Capillary Depletion

This method measures the distribution of products between the cerebral parenchyma and endothelial cells. Capillary depletion is measured after 60 seconds perfusion followed by 30 seconds rinsing. Distribution volumes (Vd) in endothelial cells and the cerebral parenchyma are expressed in µl/g.

Figure 11:
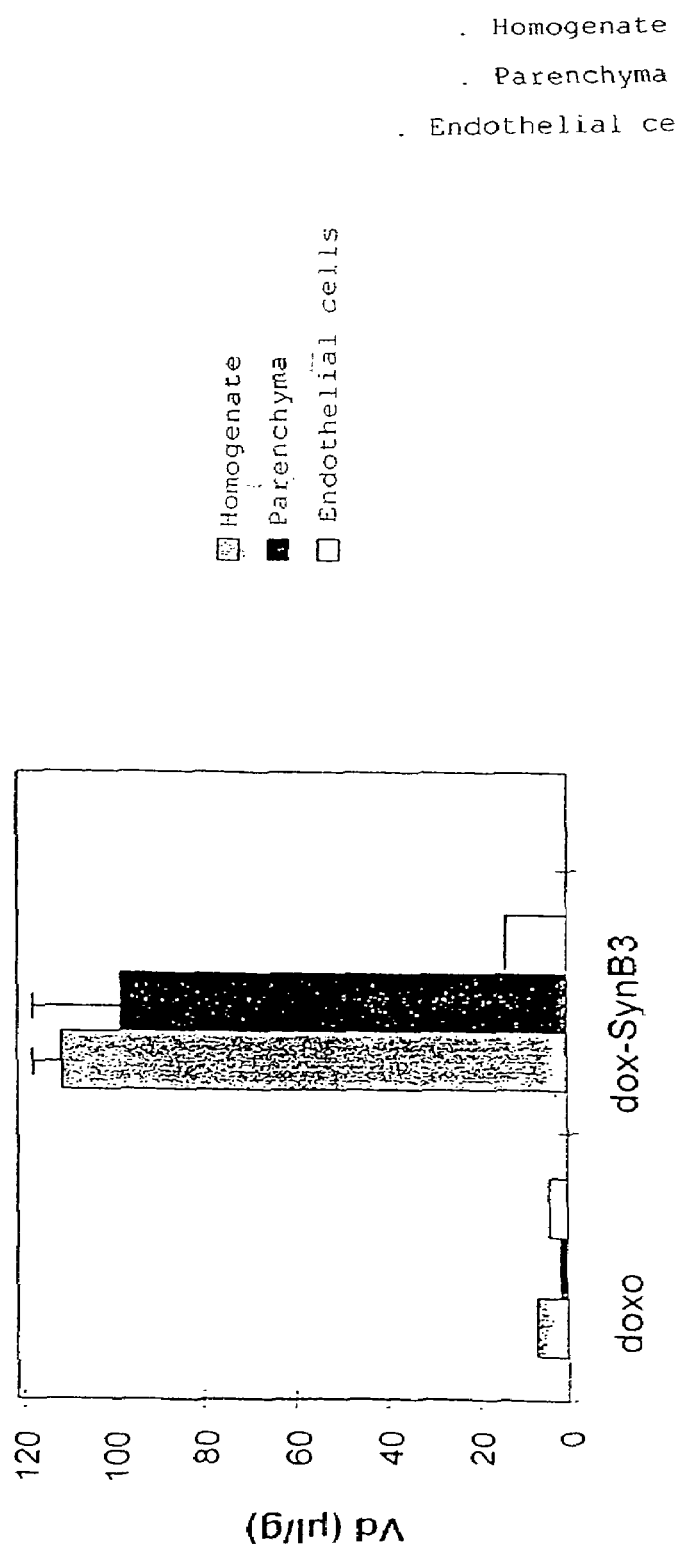
FIG. 11 shows product distribution of doxorubicin and dox-SynB3 into the brain after capillary depletion.

FIG. 11 shows that Vd in the cerebral parenchyma for free doxorubicin is 1.75 µl/g, and is 98.32 µl/g for vectorised doxorubucin. This indicates that penetration of vectorised doxorubicin in the cerebral parenchyma is 50 times greater than would be possible for free doxorubicin.

EXAMPLE IV

Penetration of Penicillin

1) Products Tested

The products tested in this example are shown in table VII below.

TABLE IX

| Compound | | SEQ ID NO: |
|---|---|---|
| PNC No. 6: PNC-SynB1 | Benzylpenicillin PNC-linker-RGGRLSYSRRRFSTSTGR | RGGRLSYSRRRFSTSTGR (SEQ ID NO:11) |

Figure 12:
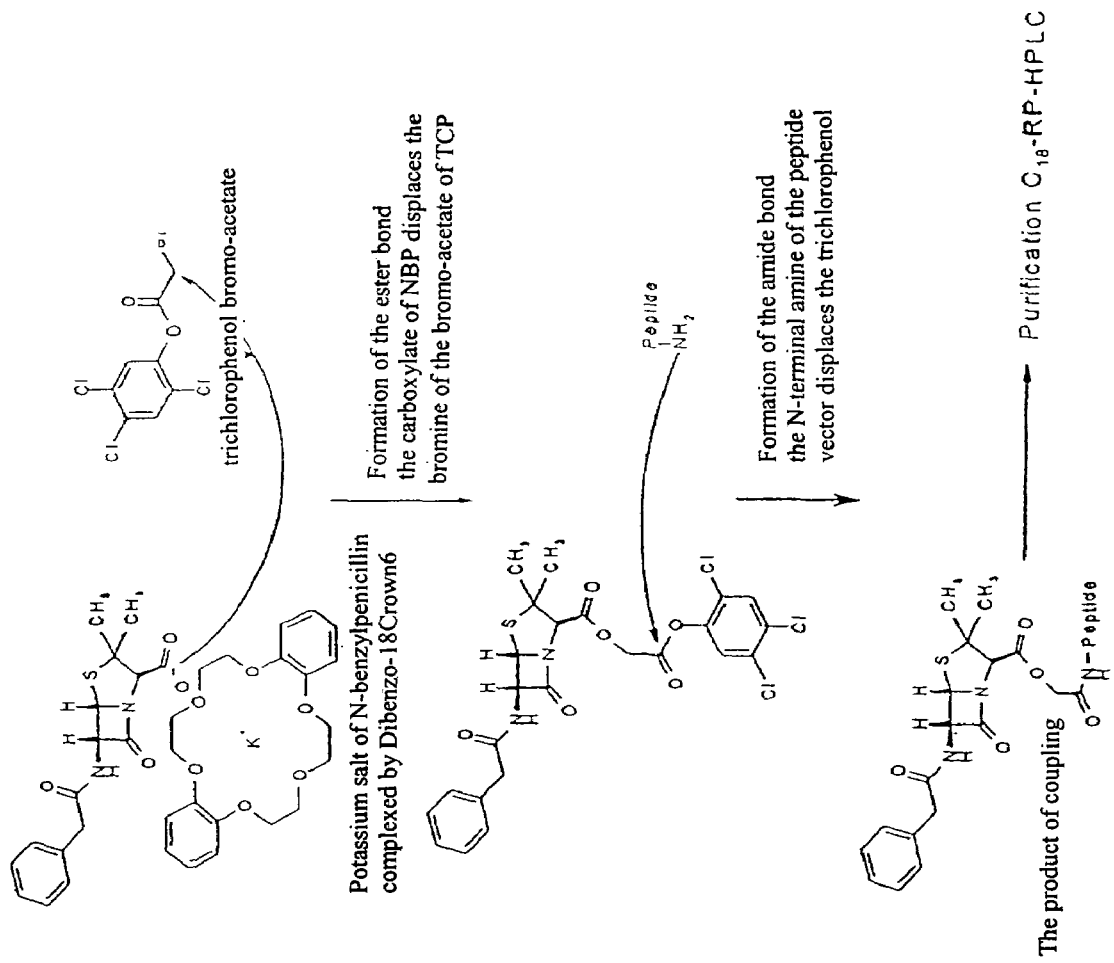
FIG. 12 shows synthesis of N-benzyl-penicillin-SynB1.

The coupling system of benzylpenicillin with the SynB1 vector is shown in FIG. 12. NBP (N-benzyl penicillin) was coupled with the SynB1 vector by a glycolamidic link. In the first step, the free carboxylate of NBP is coupled by an ester bond onto trichlorophenol bromo-acetate. The vector is then coupled by an amide link onto its N-terminal end with a trichlorophenol departure. The coupled product is purified by chromatography on the reverse phase and is then freeze dried.

2) Penetration of Products

Figure 13:
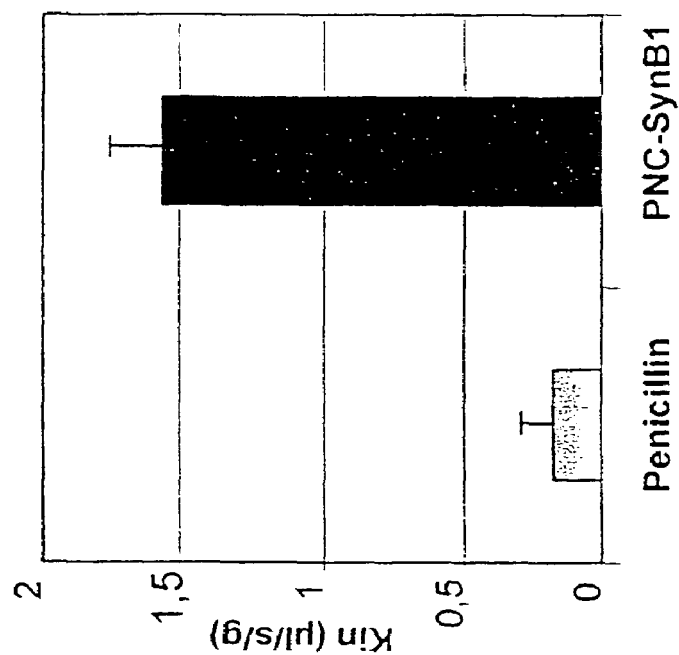
FIG. 13 shows penetration of penicillin (PNC) and PNC-SynB1 into the brain.

Penetration of benzylpenicillin alone into HEB was then compared with penetration with vectorised benzylpenicillin (compound No. 6). After 60 seconds perfusion in the buffer, penetration of radio-marked products is estimated by the influx constant or Kin in µl/sec/g. FIG. 13 shows that vectorisation of penicillin by the vector increases its transfer into the brain by a factor of about 9 times after 60 seconds perfusion in the buffer.

Figure 14:
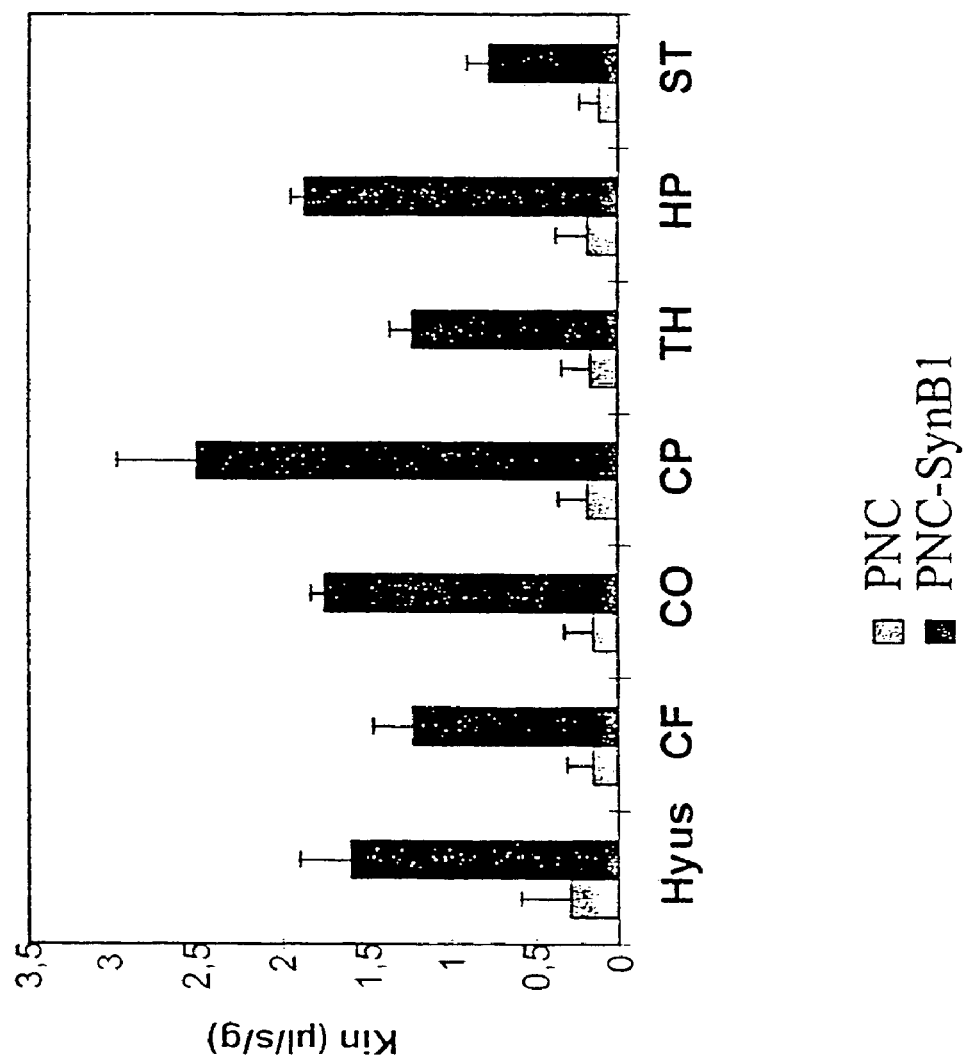
FIG. 14 shows product distribution of penicillin (PNC) and PNC-SynB1 into the brain.

In another experiment, after 30 seconds perfusion in the buffer, the brain was dissected in several regions as described above and the quantity of product in each region was measured. FIG. 14 shows that the observed penetration of compound No. 6 was six to fourteen times greater than the penetration of free penicillin, depending on the brain structure considered.

3) Distribution of Products After Capillary Depletion

This method is used to measure the distribution of products between the cerebral parenchyma and endothelial cells. Capillary depletion is done after 30 seconds perfusion followed by 30 seconds rinsing. Distribution volumes (Vd) in endothelial cells and the cerebral parenchyma are expressed in µl/g.

Figure 15:
FIG. 15 shows product distribution of penicillin (PNC) and PNC-SynB1 into the brain after capillary depletion.

FIG. 15 shows the Vd of free benzylpenicillin in the cerebral parenchyma equal to 3.94 µl/g, and the Vd for vectorised benzylpenicillin equal to 25.76 µl/g. This shows that penetration of vectorised benzylpenicillin into the cerebral parenchyma is very much increased compared with the penetration of free benzylpenicillin.

What is claimed is:

1. A method for treatment of a Central Nervous System (CNS) disease, comprising administering, to a subject suffering from a disease of the CNS, a conjugate comprising an active substance in an amount sufficient to treat said disease of the CNS, wherein the active substance is coupled directly or indirectly by a covalent bond to one of the following peptides: SynB1 (SEQ ID NO: 11) or SynB3 (SEQ ID NO: 12), and wherein said active substance is an active chemical molecule in the treatment of the CNS disease, and said disease of the CNS is selected from the group consisting of brain cancer, pain and meningitis.

2. The method of claim 1, wherein said active chemical molecule is selected from the group consisting of antitumoral agents, antibiotic agents and analgesic agents.

3. A method for driving a substance across the Blood Brain Barrier (BBB) to the Central Nervous System (CNS), comprising:

preparing a conjugate comprising an active substance coupled directly or indirectly by a covalent bond to one of the following peptides: SynB1 (SEQ ID NO: 11) or SynB3 (SEQ ID NO: 12), wherein said active substance is an active chemical molecule in the treatment of the CNS disease;

administering said conjugate to a subject suffering from a disease of the CNS in an amount sufficient to drive said active substance across the BBB to the CNS; and driving said active substance across the BBB to the CNS, wherein said disease of the CNS is selected from the group consisting of brain cancer, pain, and meningitis.

4. The method of claim 3, wherein said active chemical molecule is selected from the group consisting of antitumoral agents, antibiotic agents and analgesic agents.

* * * * *

SEQUENCE LISTING

```
<160> NUMBER OF SEQ ID NOS: 13

<210> SEQ ID NO 1
<211> LENGTH: 18
```

```
<212> TYPE: PRT
<213> ORGANISM: porcus
<220> FEATURE:
<221> NAME/KEY: PEPTIDE
<222> LOCATION: (1)..(18)
<223> OTHER INFORMATION: Protegrin PG1

<400> SEQUENCE: 1

Arg Gly Gly Arg Leu Cys Tyr Cys Arg Arg Arg Phe Cys Val Cys Val
1               5                   10                  15

Gly Arg

<210> SEQ ID NO 2
<211> LENGTH: 16
<212> TYPE: PRT
<213> ORGANISM: porcus
<220> FEATURE:
<221> NAME/KEY: PEPTIDE
<222> LOCATION: (1)..(16)
<223> OTHER INFORMATION: Protegrin PG2

<400> SEQUENCE: 2

Arg Gly Gly Arg Leu Cys Tyr Cys Arg Arg Arg Phe Cys Ile Cys Val
1               5                   10                  15

<210> SEQ ID NO 3
<211> LENGTH: 18
<212> TYPE: PRT
<213> ORGANISM: porcus
<220> FEATURE:
<221> NAME/KEY: PEPTIDE
<222> LOCATION: (1)..(18)
<223> OTHER INFORMATION: Protegrin PG3

<400> SEQUENCE: 3

Arg Gly Gly Gly Leu Cys Tyr Cys Arg Arg Arg Phe Cys Val Cys Val
1               5                   10                  15

Gly Arg

<210> SEQ ID NO 4
<211> LENGTH: 18
<212> TYPE: PRT
<213> ORGANISM: porcus
<220> FEATURE:
<221> NAME/KEY: PEPTIDE
<222> LOCATION: (1)..(18)
<223> OTHER INFORMATION: Protegrin PG4

<400> SEQUENCE: 4

Arg Gly Gly Arg Leu Cys Tyr Cys Arg Gly Trp Ile Cys Phe Cys Val
1               5                   10                  15

Gly Arg

<210> SEQ ID NO 5
<211> LENGTH: 18
<212> TYPE: PRT
<213> ORGANISM: porcus
<220> FEATURE:
<221> NAME/KEY: PEPTIDE
<222> LOCATION: (1)..(18)
<223> OTHER INFORMATION: Protegrin PG5

<400> SEQUENCE: 5

Arg Gly Gly Arg Leu Cys Tyr Cys Arg Pro Arg Phe Cys Val Cys Val
1               5                   10                  15

Gly Arg
```

```
<210> SEQ ID NO 6
<211> LENGTH: 18
<212> TYPE: PRT
<213> ORGANISM: Limmulus polyphemus
<220> FEATURE:
<221> NAME/KEY: PEPTIDE
<222> LOCATION: (1)..(18)
<223> OTHER INFORMATION: Polyphemusin P1

<400> SEQUENCE: 6

Arg Arg Trp Cys Phe Arg Val Cys Tyr Arg Gly Phe Cys Tyr Arg Lys
1               5                   10                  15

Cys Arg

<210> SEQ ID NO 7
<211> LENGTH: 18
<212> TYPE: PRT
<213> ORGANISM: Limmulus polyphemus
<220> FEATURE:
<221> NAME/KEY: PEPTIDE
<222> LOCATION: (1)..(18)
<223> OTHER INFORMATION: Polyphemusin P2

<400> SEQUENCE: 7

Arg Arg Trp Cys Phe Arg Val Cys Tyr Lys Gly Phe Cys Tyr Arg Lys
1               5                   10                  15

Cys Arg

<210> SEQ ID NO 8
<211> LENGTH: 16
<212> TYPE: PRT
<213> ORGANISM: Unknown
<220> FEATURE:
<221> NAME/KEY: MISC_FEATURE
<222> LOCATION: (1)..(16)
<223> OTHER INFORMATION: Wherein 6 to 10 Xaa residues are hydrophobic
      amino acids
<220> FEATURE:
<221> NAME/KEY: MISC_FEATURE
<222> LOCATION: (6)..(6)
<223> OTHER INFORMATION: Wherein Xaa is tryptophan

<400> SEQUENCE: 8

Xaa Xaa Xaa Xaa Xaa Xaa Xaa Xaa Xaa Xaa Xaa Xaa Xaa Xaa Xaa Xaa
1               5                   10                  15

<210> SEQ ID NO 9
<211> LENGTH: 18
<212> TYPE: PRT
<213> ORGANISM: Unknown
<220> FEATURE:
<221> NAME/KEY: MISC_FEATURE
<222> LOCATION: (1)..(1)
<223> OTHER INFORMATION: Wherein Xaa is any amino acid as defined in the
      specification. Xaa (shown/defined as B in the specification) may
      be identical or different, and represent a natural or non-natural
      amino acid, including amino acid with D configuration and
      represent an amino acid for which the side chain carries a basic
      group
<220> FEATURE:
<221> NAME/KEY: MISC_FEATURE
<222> LOCATION: (2)..(2)
<223> OTHER INFORMATION: Wherein Xaa is any amino acid as defined in the
      specification. Xaa may be identical or different, and represent a
      natural or non-natural amino acid, including amino acid with D
      configuration and represent an aliphatic or aromatic amino acid
<220> FEATURE:
<221> NAME/KEY: MISC_FEATURE
<222> LOCATION: (3)..(3)
```

-continued

```
<223> OTHER INFORMATION: Wherein Xaa is any amino acid as defined in the
      specification. Xaa may be identical or different, and represent a
      natural or non-natural amino acid, including amino acid with D
      configuration and represent an aliphatic or aromatic amino acid
<220> FEATURE:
<221> NAME/KEY: MISC_FEATURE
<222> LOCATION: (4)..(4)
<223> OTHER INFORMATION: Wherein Xaa is any amino acid as defined in the
      specification. Xaa (shown/defined as B in the specification) may
      be identical or different, and represent a natural or non-natural
      amino acid, including amino acid with D configuration and
      represent an amino acid for which the side chain carries a basic
      group
<220> FEATURE:
<221> NAME/KEY: MISC_FEATURE
<222> LOCATION: (5)..(5)
<223> OTHER INFORMATION: Wherein Xaa is any amino acid as defined in the
      specification. Xaa may be identical or different, and represent a
      natural or non-natural amino acid, including amino acid with D
      configuration and represent an aliphatic or aromatic amino acid
<220> FEATURE:
<221> NAME/KEY: MISC_FEATURE
<222> LOCATION: (6)..(6)
<223> OTHER INFORMATION: Wherein Xaa is any amino acid as defined in the
      specification. Xaa may be identical or different, and represent a
      natural or non-natural amino acid, including amino acid with D
      configuration and represent an aliphatic or aromatic amino acid
<220> FEATURE:
<221> NAME/KEY: MISC_FEATURE
<222> LOCATION: (7)..(7)
<223> OTHER INFORMATION: Wherein Xaa is any amino acid as defined in the
      specification. Xaa may be identical or different, and represent a
      natural or non-natural amino acid, including amino acid with D
      configuration and represent an aliphatic or aromatic amino acid
<220> FEATURE:
<221> NAME/KEY: MISC_FEATURE
<222> LOCATION: (8)..(8)
<223> OTHER INFORMATION: Wherein Xaa is any amino acid as defined in the
      specification. Xaa may be identical or different, and represent a
      natural or non-natural amino acid, including amino acid with D
      configuration and represent an aliphatic or aromatic amino acid
<220> FEATURE:
<221> NAME/KEY: MISC_FEATURE
<222> LOCATION: (9)..(9)
<223> OTHER INFORMATION: Wherein Xaa is any amino acid as defined in the
      specification. Xaa (shown/defined as B in the specification) may
      be identical or different, and represent a natural or non-natural
      amino acid, including amino acid with D configuration and
      represent an amino acid for which the side chain carries a basic
      group
<220> FEATURE:
<221> NAME/KEY: MISC_FEATURE
<222> LOCATION: (10)..(10)
<223> OTHER INFORMATION: Wherein Xaa is any amino acid as defined in the
      specification. Xaa (shown/defined as B in the specification) may
      be identical or different, and represent a natural or non-natural
      amino acid, including amino acid with D configuration and
      represent an amino acid for which the side chain carries a basic
      group
<220> FEATURE:
<221> NAME/KEY: MISC_FEATURE
<222> LOCATION: (11)..(11)
<223> OTHER INFORMATION: Wherein Xaa is any amino acid as defined in the
      specification. Xaa (shown/defined as B in the specification) may
      be identical or different, and represent a natural or non-natural
      amino acid, including amino acid with D configuration and
      represent an amino acid for which the side chain carries a basic
      group
<220> FEATURE:
<221> NAME/KEY: MISC_FEATURE
<222> LOCATION: (12)..(12)
<223> OTHER INFORMATION: Wherein Xaa is any amino acid as defined in the
      specification. Xaa may be identical or different, and represent a
      natural or non-natural amino acid, including amino acid with D
      configuration and represent an aliphatic or aromatic amino acid
<220> FEATURE:
<221> NAME/KEY: MISC_FEATURE
<222> LOCATION: (13)..(13)
<223> OTHER INFORMATION: Wherein Xaa is any amino acid as defined in the
```

```
                    specification. Xaa may be identical or different, and represent a
                    natural or non-natural amino acid, including amino acid with D
                    configuration and represent an aliphatic or aromatic amino acid
<220> FEATURE:
<221> NAME/KEY: MISC_FEATURE
<222> LOCATION: (14)..(14)
<223> OTHER INFORMATION: Wherein Xaa is any amino acid as defined in the
                    specification. Xaa may be identical or different, and represent a
                    natural or non-natural amino acid, including amino acid with D
                    configuration and represent an aliphatic or aromatic amino acid
<220> FEATURE:
<221> NAME/KEY: MISC_FEATURE
<222> LOCATION: (15)..(15)
<223> OTHER INFORMATION: Wherein Xaa is any amino acid as defined in the
                    specification. Xaa may be identical or different, and represent a
                    natural or non-natural amino acid, including amino acid with D
                    configuration and represent an aliphatic or aromatic amino acid
<220> FEATURE:
<221> NAME/KEY: MISC_FEATURE
<222> LOCATION: (16)..(16)
<223> OTHER INFORMATION: Wherein Xaa is any amino acid as defined in the
                    specification. Xaa may be identical or different, and represent a
                    natural or non-natural amino acid, including amino acid with D
                    configuration and represent an aliphatic or aromatic amino acid
<220> FEATURE:
<221> NAME/KEY: MISC_FEATURE
<222> LOCATION: (17)..(17)
<223> OTHER INFORMATION: Wherein Xaa is any amino acid as defined in the
                    specification. Xaa may be identical or different, and represent a
                    natural or non-natural amino acid, including amino acid with D
                    configuration and represent an aliphatic or aromatic amino acid
<220> FEATURE:
<221> NAME/KEY: MISC_FEATURE
<222> LOCATION: (18)..(18)
<223> OTHER INFORMATION: Wherein Xaa is any amino acid as defined in the
                    specification. Xaa (shown/defined as B in the specification) may
                    be identical or different, and represent a natural or non-natural
                    amino acid, including amino acid with D configuration and
                    represent an amino acid for which the side chain carries a basic
                    group
<220> FEATURE:
<221> NAME/KEY: PEPTIDE
<222> LOCATION: (1)..(18)
<223> OTHER INFORMATION: Peptide of formula (II)

<400> SEQUENCE: 9

Xaa Xaa Xaa Xaa Xaa Xaa Xaa Xaa Xaa Xaa Xaa Xaa Xaa Xaa Xaa Xaa
1               5                   10                  15

Xaa Xaa

<210> SEQ ID NO 10
<211> LENGTH: 17
<212> TYPE: PRT
<213> ORGANISM: Unknown
<220> FEATURE:
<221> NAME/KEY: MISC_FEATURE
<222> LOCATION: (1)..(1)
<223> OTHER INFORMATION: Wherein Xaa is any amino acid as defined in the
                    specification. Xaa (shown/defined as B in the specification) may
                    be identical or different, and represent a natural or non-natural
                    amino acid, including amino acid with D configuration and
                    represent an amino acid for which the side chain carries a basic
                    group
<220> FEATURE:
<221> NAME/KEY: MISC_FEATURE
<222> LOCATION: (2)..(2)
<223> OTHER INFORMATION: Wherein Xaa is any amino acid as defined in the
                    specification. Xaa may be identical or different, and represent a
                    natural or non-natural amino acid, including amino acid with D
                    configuration and represent an aliphatic or aromatic amino acid
<220> FEATURE:
<221> NAME/KEY: MISC_FEATURE
<222> LOCATION: (3)..(3)
<223> OTHER INFORMATION: Wherein Xaa is any amino acid as defined in the
                    specification. Xaa may be identical or different, and represent a
                    natural or non-natural amino acid, including amino acid with D
```

-continued

```
      configuration and represent an aliphatic or aromatic amino acid
<220> FEATURE:
<221> NAME/KEY: MISC_FEATURE
<222> LOCATION: (4)..(4)
<223> OTHER INFORMATION: Wherein Xaa is any amino acid as defined in the
      specification. Xaa may be identical or different, and represent a
      natural or non-natural amino acid, including amino acid with D
      configuration and represent an aliphatic or aromatic amino acid
<220> FEATURE:
<221> NAME/KEY: MISC_FEATURE
<222> LOCATION: (5)..(5)
<223> OTHER INFORMATION: Wherein Xaa is any amino acid as defined in the
      specification. Xaa (shown/defined as B in the specification) may
      be identical or different, and represent a natural or non-natural
      amino acid, including amino acid with D configuration and
      represent an amino acid for which the side chain carries a basic
      group
<220> FEATURE:
<221> NAME/KEY: MISC_FEATURE
<222> LOCATION: (6)..(6)
<223> OTHER INFORMATION: Wherein Xaa is any amino acid as defined in the
      specification. Xaa may be identical or different, and represent a
      natural or non-natural amino acid, including amino acid with D
      configuration and represent an aliphatic or aromatic amino acid
<220> FEATURE:
<221> NAME/KEY: MISC_FEATURE
<222> LOCATION: (7)..(7)
<223> OTHER INFORMATION: Wherein Xaa is any amino acid as defined in the
      specification. Xaa may be identical or different, and represent a
      natural or non-natural amino acid, including amino acid with D
      configuration and represent an aliphatic or aromatic amino acid
<220> FEATURE:
<221> NAME/KEY: MISC_FEATURE
<222> LOCATION: (8)..(8)
<223> OTHER INFORMATION: Wherein Xaa is any amino acid as defined in the
      specification. Xaa may be identical or different, and represent a
      natural or non-natural amino acid, including amino acid with D
      configuration and represent an aliphatic or aromatic amino acid
<220> FEATURE:
<221> NAME/KEY: MISC_FEATURE
<222> LOCATION: (9)..(9)
<223> OTHER INFORMATION: Wherein Xaa is any amino acid as defined in the
      specification. Xaa (shown/defined as B in the specification) may
      be identical or different, and represent a natural or non-natural
      amino acid, including amino acid with D configuration and
      represent an amino acid for which the side chain carries a basic
      group
<220> FEATURE:
<221> NAME/KEY: MISC_FEATURE
<222> LOCATION: (10)..(10)
<223> OTHER INFORMATION: Wherein Xaa is any amino acid as defined in the
      specification. Xaa may be identical or different, and represent a
      natural or non-natural amino acid, including amino acid with D
      configuration and represent an aliphatic or aromatic amino acid
<220> FEATURE:
<221> NAME/KEY: MISC_FEATURE
<222> LOCATION: (11)..(11)
<223> OTHER INFORMATION: Wherein Xaa is any amino acid as defined in the
      specification. Xaa may be identical or different, and represent a
      natural or non-natural amino acid, including amino acid with D
      configuration and represent an aliphatic or aromatic amino acid
<220> FEATURE:
<221> NAME/KEY: MISC_FEATURE
<222> LOCATION: (12)..(12)
<223> OTHER INFORMATION: Wherein Xaa is any amino acid as defined in the
      specification. Xaa may be identical or different, and represent a
      natural or non-natural amino acid, including amino acid with D
      configuration and represent an aliphatic or aromatic amino acid
<220> FEATURE:
<221> NAME/KEY: MISC_FEATURE
<222> LOCATION: (13)..(13)
<223> OTHER INFORMATION: Wherein Xaa is any amino acid as defined in the
      specification. Xaa may be identical or different, and represent a
      natural or non-natural amino acid, including amino acid with D
      configuration and represent an aliphatic or aromatic amino acid
<220> FEATURE:
<221> NAME/KEY: MISC_FEATURE
<222> LOCATION: (14)..(14)
<223> OTHER INFORMATION: Wherein Xaa is any amino acid as defined in the
```

```
          specification. Xaa (shown/defined as B in the specification) may
          be identical or different, and represent a natural or non-natural
          amino acid, including amino acid with D configuration and
          represent an amino acid for which the side chain carries a basic
          group
<220> FEATURE:
<221> NAME/KEY: MISC_FEATURE
<222> LOCATION: (15)..(15)
<223> OTHER INFORMATION: Wherein Xaa is any amino acid as defined in the
          specification. Xaa (shown/defined as B in the specification) may
          be identical or different, and represent a natural or non-natural
          amino acid, including amino acid with D configuration and
          represent an amino acid for which the side chain carries a basic
          group
<220> FEATURE:
<221> NAME/KEY: MISC_FEATURE
<222> LOCATION: (16)..(16)
<223> OTHER INFORMATION: Wherein Xaa is any amino acid as defined in the
          specification. Xaa may be identical or different, and represent a
          natural or non-natural amino acid, including amino acid with D
          configuration and represent an aliphatic or aromatic amino acid
<220> FEATURE:
<221> NAME/KEY: MISC_FEATURE
<222> LOCATION: (17)..(17)
<223> OTHER INFORMATION: Wherein Xaa is any amino acid as defined in the
          specification. Xaa (shown/defined as B in the specification) may
          be identical or different, and represent a natural or non-natural
          amino acid, including amino acid with D configuration and
          represent an amino acid for which the side chain carries a basic
          group
<220> FEATURE:
<221> NAME/KEY: PEPTIDE
<222> LOCATION: (1)..(17)
<223> OTHER INFORMATION: Peptide of formula (III)

<400> SEQUENCE: 10

Xaa Xaa Xaa Xaa Xaa Xaa Xaa Xaa Xaa Xaa Xaa Xaa Xaa Xaa Xaa Xaa
1               5                   10                  15

Xaa

<210> SEQ ID NO 11
<211> LENGTH: 18
<212> TYPE: PRT
<213> ORGANISM: Unknown
<220> FEATURE:
<221> NAME/KEY: PEPTIDE
<222> LOCATION: (1)..(18)
<223> OTHER INFORMATION: Syn B1

<400> SEQUENCE: 11

Arg Gly Gly Arg Leu Ser Tyr Ser Arg Arg Arg Phe Ser Thr Ser Thr
1               5                   10                  15

Gly Arg

<210> SEQ ID NO 12
<211> LENGTH: 10
<212> TYPE: PRT
<213> ORGANISM: Unknown
<220> FEATURE:
<221> NAME/KEY: PEPTIDE
<222> LOCATION: (1)..(10)
<223> OTHER INFORMATION: Syn B3

<400> SEQUENCE: 12

Arg Arg Leu Ser Tyr Ser Arg Arg Arg Phe
1               5                   10

<210> SEQ ID NO 13
<211> LENGTH: 17
<212> TYPE: PRT
<213> ORGANISM: Unknown
```

```
<220> FEATURE:
<221> NAME/KEY: PEPTIDE
<222> LOCATION: (1)..(17)
<223> OTHER INFORMATION: Peptide with amino acids in D form

<400> SEQUENCE: 13

Arg Gln Ile Lys Ile Trp Phe Gln Asn Arg Arg Met Lys Trp Lys
1               5                   10                  15

Lys
```